United States Patent
Zhang (10) Patent No.: US 11,124,561 B2
(45) Date of Patent: Sep. 21, 2021

(54) BROADLY CROSS-REACTIVE HIV-1-SPECIFIC ANTIBODIES FOR PREVENTION AND TREATMENT OF HIV

(71) Applicant: THE UNIVERSITY OF HONG KONG, Hong Kong (CN)

(72) Inventor: Mei-Yun Zhang, Hong Kong (HK)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 16/291,475

(22) Filed: Mar. 4, 2019

(65) Prior Publication Data

US 2019/0185549 A1    Jun. 20, 2019

Related U.S. Application Data

(62) Division of application No. 13/534,834, filed on Jun. 27, 2012, now Pat. No. 10,280,213.

(60) Provisional application No. 61/504,586, filed on Jul. 5, 2011.

(51) Int. Cl.
C07K 16/10 (2006.01)
C07K 14/16 (2006.01)

(52) U.S. Cl.
CPC ........ *C07K 16/1063* (2013.01); *C07K 14/162* (2013.01); *C07K 2317/21* (2013.01); *C07K 2317/32* (2013.01); *C07K 2317/55* (2013.01); *C07K 2317/75* (2013.01); *C07K 2317/76* (2013.01); *C12N 2740/16111* (2013.01)

(58) Field of Classification Search
CPC .............. C07K 16/1063; C07K 14/162; C07K 2317/55; C12N 2740/16111
See application file for complete search history.

(56) References Cited

U.S. PATENT DOCUMENTS

2008/0038280 A1    2/2008    Dimitrov et al.

FOREIGN PATENT DOCUMENTS

WO    WO-2006044410 A2    4/2006

OTHER PUBLICATIONS

Wyatt, R., et al., Sep. 1995, Involvement of the V1/V2 variable loop structure in the exposure of human immunodeficiency virus type 1 gp120 epitopes induced by receptor binding, J. Virol. 69(9):5723-5733.*
Moulard, M., et al., May 2002, Broadly cross-reactive HIV-1-neutralizing human monoclonal Fab selected for binding to gp120-CD4-CCR5 complexes, Proc. Natl. Acad. Sci. 99(10):6913-6918.*
Zhang, M.-Y., et al., 2004, Improved breadth and potency of an HIV-1-neutralizing human single-chain antibody by random mutagenesis and sequential antigen panning, J. Mol. Biol. 335:209-219.*
Decker et al., "Antigenic conservation and immunogenicity of the HIV coreceptor biding site", *J Exp Med*, May 2, 2005, 201(9), pp. 1,407-1,419.
Labrijin et al., "Access of antibody molecules to the conserved coreceptor biding site on glycoprotein gp120 is sterically restricted on primary human immunodeficiency virus type 1", *J Virol*, Oct. 2003, 77(19), pp. 10,557-10,565.
Xiao et al., "Germline-like predeccessors of broadly neutralizing antibodies lack measurable binding to HIV-1 envelope glycoproteins: implications for evasion of immune responses and design of vaccine immunogens", *Biochem Biophys Res Commun*, Dec. 18, 2009, 390(3), pp. 404-409.
Xiao et al., "Maturation Pathways of Cross-Reactive HIV-1 Neutralizing Antibodies", *Viruse*, 2009, 1, pp. 802-817.
Bansal, Geetha P. "A summary of the workshop on passive immunization using monoclonal antibodies for HIV/AIDS, held at the National Institute of Allergy and Infectious Diseases, Bethesda, Mar. 10, 2006." Biologicals 35.4 (2007): 367-371.
West, Anthony P., et al. "Single-chain Fv-based anti-HIV proteins: potential and limitations." *Journal of virology* 86.1 (2012): 195-202.
Choudhry, Vidita, et al. "Antibody-based inhibitors of HIV infection." Expert opinion on biological therapy 6.5 (2006): 523-531.
West Jr, Anthony P., et al. "Structural insights on the role of antibodies in HIV-1 vaccine and therapy." Cell 156.4 (2014): 633-648.
Li, Yucheng, et al. "The I Binding Specificity of Human VH4-34 (VH4-21) Encoded Antibodies is Determined by Both VH Framework Region 1 and Complementarity Determining Region 3." Journal of molecular biology 256.3 (1996): 577-589.
Winkler, Karsten, et al. "Changing the antigen binding specificity by single point mutations of an anti-p24 (HIV-1) antibody." The Journal of Immunology 165.8 (2000): 4505-4514.
USPTO Written Description Guidelines Training Materials dated Mar. 25, 2008, "Example 13: Antibodies to a Single Protein".
Wyatt, Richard, et al. "Involvement of the V1/V2 variable loop structure in the exposure of human immunodeficiency virus type 1 gp120 epitopes induced by receptor binding." Journal of virology 69.9 (1995): 5723-5733.
Liao, Hua-Xin, et al. "Immunogenicity of constrained monoclonal antibody A32-human immunodeficiency virus (HIV) Env gp120 complexes compared to that of recombinant HIV type 1 gp120 envelope glycoproteins." Journal of virology 78.10 (2004): 5270-5278.
Boots, Lynn J., et al. "Anti-human immunodeficiency virus type 1 human monoclonal antibodies that bind discontinuous epitopes in the viral glycoproteins can identify mimotopes from recombinant phage peptide display libraries." AIDS research and human retroviruses 13.18 (1997): 1549-1559.

* cited by examiner

*Primary Examiner* — Jeffrey S Parkin
(74) *Attorney, Agent, or Firm* — Leason Ellis LLP (57) ABSTRACT

Provided herein are HIV-1-specific transforming antibodies (tAbs) and antigens that are recognized by HIV-1-specific tAbs. Also provided herein are methods for screening and/or generating HIV-1-specific tAbs and uses of tAbs for prevention and treatment of HIV-1 infection.

12 Claims, 3 Drawing Sheets

Specification includes a Sequence Listing.

A32 LC: (SEQ ID NO. 1)
QSALTQPPSASGSPGQSVTISCTGTSSDVGGYNYVSWYQHHPGKAPKLIISEVNNRPSGVPDRFSGSKSGNTASLTV
SGLQAEDEAEYYCSSYTDIHNFVFGGGTKVTVLGQPKANPTVTLFPPSSEELQANKATLVCLISDFYPGAVTVAWKA
DSSPVKAGVETTTPSKQSNNKYAASSYLSLTPEQWKSHKSYSCQVTHEGSTVEKTV

A32 Fd: (SEQ ID NO. 2)
QVQLQQWGPGLVKPSQTLSLSCTVSGGSSSSGAHYWSWIRQYPGKGLEWIGYIHYSGNTYYNPSLKSRITISQHTSE
NQFSLKLNSVTVADTAVYYCARGTRLRTLRNAFDIWGQGTTVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTS

Amino acid sequence of human A32

FIG. 3

BROADLY CROSS-REACTIVE HIV-1-SPECIFIC ANTIBODIES FOR PREVENTION AND TREATMENT OF HIV

CROSS-REFERENCE TO RELATED PATENT APPLICATIONS

This application claims priority to U.S. patent application Ser. No. 13/534,834, filed Jun. 27, 2012, which claims the benefit of priority under 35 U.S.C. Section 119(e) of U.S. Provisional Application No. 61/504,586 filed Jul. 5, 2011, both of which are incorporated by reference in their entireties as part of the present application.

1. BACKGROUND

Human immunodeficiency virus type I (HIV-1) has contributed to an estimated 40 million deaths since it was first recognized in 1981. Currently, over 30 million people worldwide are living with the virus. The development of effective HIV-1 vaccine immunogens that can elicit high titer, potent, and broadly neutralizing antibodies (bnAbs) remains a major challenge.

Entry of HIV-1 into target cells is mediated by binding of highly conserved epitopes on HIV envelope glycoproteins (Env) to a primary cell-surface receptor CD4. Binding of Env to CD4 initiates a series of conformational changes of the Env structure, leading to exposure and/or formation of coreceptor binding sites that are recognized by cell surface co-receptors (e.g. chemokine receptors CCR5 or CXCR4). To evade human immune surveillance, HIV-1 has evolved a variety of strategies, including rapid generation of genetic variants and hiding of conserved epitopes on envelope glycoproteins (Env) by variable loops, heavy glycosylation, oligomerization and conformational masking.

HIV-1 Env-specific antibodies can be categorized into two major groups: the surface domain gp120-specific Abs and the transmembrane domain gp41-specific Abs. Anti-gp120 Abs include CD4 binding site (CD4bs) Abs, CD4-induced (CD4i) Abs and Abs against other regions of gp120. These antibodies are believed to act, at least in part, by binding to the exposed Env surface and obstructing the initial interaction between a trimeric array of gp120 molecules on the virion surface and receptor molecules on the target cells (see, e.g., Parren et al., *Adv. Immunol.*, 77, 195-262 (2001); Parren et al., *J. Virol.*, 72, 3512-3519 (1998); and Ugolini et al., *J. Exp. Med.*, 186, 1287-1298 (1997)).

Although CD4bs Abs (e.g. b12) that bind to the CD4 binding site on gp120 can potently neutralize certain HIV strains, resistant variants emerge quickly and thereby significantly reduce the anti-viral effects of CD4bs Abs. CD4i Abs, the most abundant Abs in Env-immunized and HIV-1-infected individuals, recognize the conserved coreceptor binding site on gp120. Before binding of CD4 to HIV Env, access to the coreceptor binding site by the full length CD4i Abs is sterically hindered. As a result, the full length CD4i Abs can not or only weakly neutralize HIV-1 prior to CD4-binding. In the presence of CD4, CD4i Abs potently and broadly neutralize a variety of clades of HIV-1 primary isolates as well as genetically divergent HIV-2.

Although soluble CD4 (sCD4) can be useful for enhancing neutralization activity of CD4i Abs, it suffers from several major limitations. First, some HIV-1 isolates are CD4-independent. In addition, sCD4 cannot neutralize HIV-1 primary isolates, suggesting that sCD4 may not bind to the native envelope spike on the viral surface of primary isolates. Further, sCD4 has a significantly short serum half-life compared to antibodies. Moreover, there is a concern that CD4 constructs may deplete CD4-positive T cells in vivo.

It is believed that potent broadly neutralizing antibodies (bnAbs) can serve as a promising candidate for prevention and treatment of HIV-1 infection. bnAbs, which are rarely found in HIV-infected individuals, may slow or delay the progression of HIV-1 infection. An estimated 1% natural infections lead to long-term no disease progression without treatment. Among these long-term nonprogressors (LTNPs), about 30% have high titres of bnAbs. Polyclonal antibodies (pAbs) purified from sera of these LTNPs have shown to produce certain desirable treatment effects on HIV-1-infected patients.

However, monoclonal antibodies (mAbs) isolated from LTNPs only exhibited weak or modest neutralizing activity. A mixture of the isolated mAbs did not show neutralization potency and breadth that are comparable to those of the pAbs. Even for a handful of mAbs that exhibit in vitro broadly neutralizing human monoclonal antibodies (bnmAbs), such as anti-gp120 mAbs b12 and 2G12 and anti-gp41 mAbs 2F5 and 4E10, none of them resulted in satisfactory in vivo efficacy in human clinical trials. Furthermore, currently available mAbs such as b12, 2F5, and 4E10 are shown to possess autoimmune reactivity, including binding to self antigens such as dsDNA, cardiolipin, and phosphotidylserine.

Since HIV-1 was first discovered more than two decades ago, conventional vaccine strategies have failed to develop effective vaccine candidates that can elicit potent broadly cross-reactive HIV-1-neutralizing antibodies. There continues to be a pressing need for novel HIV vaccine strategies and compositions that can control the spread of HIV/AIDS pandemic.

2. SUMMARY

The aforementioned need is satisfied by providing HIV-1-specific transforming antibodies (tAbs), and fragments and fusion constructs thereof that bind to one or more epitopes of native HIV envelope glycoprotein (Env). HIV-1-specific tAbs provided herein significantly enhance neutralization activity of a second antibody (e.g. CD4-induced antibody) against a broad range of HIV clades. Also embodied are epitopes, peptides, antigens, antigenic fragments, and/or fusion constructs that are recognized, at least in part, by tAbs provided herein.

Also provided herein are methods for generating HIV-1-specific tAbs that induce significant neutralization of HIV isolates. HIV-1-specific tAbs provided herein can be generated by screening a library of antibodies that bind to native HIV envelope glycoproteins, and selecting the antibody that enhances the binding affinity and/or neutralization activity of a second antibody such as CD4i Abs.

Also provided herein are therapeutic compositions, comprising a therapeutically effective amount of HIV-1-specific tAbs and antigens provided herein. In an embodiment, the compositions can be used as a vaccine composition to prevent individuals from acquiring HIV infection. In another embodiment, the compositions can be used to treat or ameliorate HIV infection.

4. DETAILED DISCLOSURE

Provided herein are HIV-1-specific transforming antibodies (tAbs), and fragments and fusion constructs thereof that bind to one or more epitopes of native HIV envelope glycoproteins (Env). Advantageously, tAbs disclosed herein significantly enhance neutralization activity of a second antibody (e.g. CD4-induced antibody) against a broad range of HIV clades. Also embodied are antigens, antigenic fragments, and/or fusion constructs that are recognized, at least in part, by tAbs of the present invention.

Also provided herein are methods for generating HIV-1-specific tAbs that induce significant neutralization of HIV isolates. HIV-1-specific tAbs provided herein can be generated by screening a library of antibodies that bind to native HIV envelope glycoproteins, and selecting the antibody that enhances binding affinity and/or neutralization activity of the second antibody.

Further provided herein are therapeutic compositions, comprising a therapeutically effective amount of HIV-1-specific tAbs and antigens of the present invention, useful for treatment and/or prevention of HIV infection. In an embodiment, the compositions provided herein can be used as a vaccine composition to prevent individuals from acquiring HIV infection. In another embodiment, the compositions provided herein can be used to treat or ameliorate HIV infection.

It is contemplated that HIV LTNPs patients who have high titers of HIV-1-specific broadly cross-reactive mAbs also possess tAbs that bind to the trimeric spikes of the virion envelope. Binding tAbs to the HIV Env forms a tAb-Env complex. Formation of the tAb-Env complex induces significant conformational changes of the Env structure, leading to formation and exposure of a binding site for a second antibody (e.g. CD4i) that neutralizes against a broad range of HIV isolates. The tAb-induced conformational change results in significantly increased sensitivity of the virus to other HIV-specific antibodies, e.g. CD4-induced (CD4i) Abs. It is further contemplated that tAbs provided herein can synergistically enhance the neutralization activity of antibodies such as CD4i Abs.

In a preferred embodiment, the second antibody that can neutralize against a variety of HIV clades is a CD4i antibody. Using sequential antigen panning and competitive antigen panning methodologies, HIV-1-specific broadly cross-reactive mAbs are isolated from sera of LTNPs. For LTNPs whose sera have high titers of bnAbs, several panels of CD4bs Abs, CD4i Abs, and gp41-specific Abs are also identified. Among these antibodies, CD4bs Abs exhibited potent HIV-1-neutralizing activity and neutralized HIV-1 isolates from different clades. In one embodiment, the second antibody is a gp41-specific Abs. CD4i Abs represent the most potent bnmAbs. In one embodiment, the second antibody is a single chain antibody fragment (scFv). In one embodiment, the bnmAbs is scFv m9 isolated from scFv X5 mutant library by sequential antigen panning. In one embodiment, the antibody is a full-length CD4i Abs (eg. IgG X5). In one embodiment, both CD4i germline and mature single chain antibodies bind to and neutralize HIV-1 isolates. In some embodiments, other neutralizing HIV-1 antibodies, such as CD4bs Abs and the germline Abs, do not bind to HIV-1 Env or neutralize the virus. In certain embodiments, the second antibodies are CD4i germline Abs and CD4i mature Abs that are abundantly elicited in HIV-1 patients. In one embodiment, the second antibodies exist in uninfected humans. In certain embodiments, neutralization activity of the second antibodies are synergistically enhanced by tAbs.

HIV-1-Specific Transforming Antibodies

In one aspect, provided herein are HIV-1-specific transforming antibodies (tAbs) that bind to one or more epitopes of native HIV envelope glycoproteins (Env). In one embodiment, the Env are organized into trimeric spikes on the virion surface. Also embodied are antigens, antigenic fragments, and/or fusion constructs that are recognized, at least in part, by tAbs provided herein. In an embodiment, tAbs bind to a surface glycoprotein-glycoprotein 120 (gp120). In one embodiment, tAbs bind to gp160. In one embodiment, tAbs bind to gp120/gp41 complex. In one embodiment, tAbs bind to the oligomeric forms of the gp120/gp41 complex. In one embodiment, binding of tAb induces conformational changes in the Env structure, leading to exposure and/or (gp41) formation of a binding site for a second antibody that can significantly neutralize HIV isolates. In one embodiment, tAbs bind to the ectodomain of gp41. In one embodiment, tAbs bind to a portion of a trimer of two interacting regions of gp41. In a specific embodiment, tAbs bind to a portion of the six helix bundle that consists of an interior parallel coiled-coil trimer (region one) and/or the three α-helixes (region two). In one embodiment, tAbs bind to a portion of DP-107 or DP-178. In one embodiment, provided herein are tAbs that are broadly cross-reactive and induce significant neutralization activity of secondary antibodies against a broad range of primary HIV isolates.

HIV-1-specific tAbs provided herein bind specifically to conserved regions (C1-C5) on gp120. In certain embodiments, tAbs bind specifically to conserved epitopes of variable regions (V1-V5) on gp120. In one embodiment, tAbs bind specifically to an epitope that is or overlaps with the CD4 binding site. In certain embodiments, epitopes recognized by tAbs are highly conserved and do not involve or overlap with A32 binding sites. In one embodiment, A32 epitope does not overlap the CD4 binding site.

In one embodiment, binding of tAbs forms a tAb-Env complex and induces conformational changes in the Env structure. In one embodiment, binding of the tAbs leads to greater exposure and/or formation of a second antibody binding site that is hidden or unformed before tAb-binding. In one embodiment, tAb-binding removes the steric occlusion between the tAb-anchored viral spike and the second antibody binding site, reorient residues on the virion surface that mask the conserved second antibody binding site, or otherwise rearrange the Env structure to enhance binding efficiency of the second antibody.

In one embodiment, binding of tAbs leads to significantly increased binding affinity and neutralization activity of the second antibody. In certain embodiments, the increase in binding affinity is about 2-fold or greater, e.g., at least about 2-fold, 3-fold, 4-fold, 5-fold, 6-fold, 7-fold, 8-fold, 9-fold, or 10-fold. In certain embodiments, tAb-binding reduces $IC_{50}$ and/or $EC_{50}$ of the second antibody by about 2-fold or greater, e.g., at least about 2-fold, 3-fold, 4-fold, 5-fold, 6-fold, 7-fold, 8-fold, 9-fold, or 10-fold. In a specific embodiment, tAb-binding leads to equivalent or increased binding affinity and/or neutralization activity for the second antibody than that which is induced by CD4, sCD4, or A32. In one embodiment, tAb-induced increase in binding affinity and/or neutralization activity of the second antibody is about 2-fold or greater, e.g., at least about 2-fold, 3-fold, 4-fold, 5-fold, 6-fold, 7-fold, 8-fold, 9-fold, or 10-fold, as compared to that induced by CD4, sCD4, or A32.

The term "binding specificity," "specificity," "specifically reacts," or "specifically interacts," as used herein, refers to the ability of an antibody or other agent to detectably bind an epitope presented on an antigen, such as an epitope of HIV-1 gp120, while having relatively little detectable reactivity with other proteins or structures. In one embodiment, specificity can be relatively determined by binding or competitive assays. In one embodiment, specificity is determined using e.g., Biacore instruments. In one embodiment, specificity is exhibited by, e.g., about 10:1, about 20:1, about 50:1, about 100:1, about 10,000:1 or greater ratio of affinity/avidity in binding to the specific antigen versus nonspecific binding to other irrelevant molecules.

The term "half maximal inhibitory concentration ($IC_{50}$)," as used herein, refers to the concentration of a substance (e.g. a compound, protein, or antibody) that is required to inhibit the activity (e.g. the ability to enter, proliferate, or infect a target cell) of HIV isolates to 50% of the level, as compared to the activity of HIV isolates that have not been contacted by the substance. The term "half maximal effective concentration ($EC_{50}$)," as used herein, refers to the concentration of a substance (e.g. a compound, protein, or antibody) where 50% of its maximal effect is achieved.

The second antibody can bind to any epitope of HIV envelope protein. In one embodiment, the second antibody binds to an epitope of gp120 envelope glycoprotein. Examples of suitable second antibodies include, but are not limited to, somatic matured and germline CD4i Abs, such as E51, 31H, 23e, 21c, 17b, 48d, Fab X5, 412d, 19e, ED47, ED49, m12, m6, and m9. Suitable second antibodies further include antibodies and fragments or fusion constructs thereof that bind to a CD4-inducible epitope of HIV Env. The term "CD4-inducible epitope," as used herein, refers to an antigenic site on HIV Env, gp120 or gp41, wherein specific binding to the antigenic site by an antibody provided herein is increased or augmented by binding of CD4 or sCD4 to HIV Env, gp120 or gp41.

In one embodiment, the second antibody is broadly cross-reactive (i.e. can bind to a broad range of HIV primary isolates from different strains and clades). In one embodiment, the second antibody induces significant neutralization against a broad range of clades, including one or more clades of HIV-1 clade A, B, C, D, E, F, G, and H. In certain embodiments, second antibodies provided herein have neutralization activity against HIV-2 and Simian immunodeficiency viruses (SIV). In one embodiment, the second antibody is a Fab X5 antibody. In one embodiment, the second antibody is an m9 antibody. The m9 antibody is an scFv fragment derived from Fab X5 by random mutagenesis and sequential antigen panning, which exhibits potent neutralization of a broad range of primary HIV-1 isolates (see, e.g., Zhang et al., *J. Mol. Biol.*, 335, 209-219 (2004)).

The HIV-1-specific tAbs provided herein have neutralizing activity against HIV viruses. In one embodiment, such neutralizing activity is synergistically enhanced in combination with the second antibody. Neutralizing antibodies provided herein include, but are not limited to, antibodies that are capable of substantially inhibiting or reducing any activity of HIV, such as for example, the entry of HIV into host cells, the fusion of viral and host cell membranes, or the replication of HIV. In one embodiment, neutralizing antibodies provided herein act, at least in part, by binding to the exposed envelope surface and preventing or obstructing the interaction between gp120 molecules on the virion surface and receptor molecules on the target cell. In one embodiment, neutralizing antibodies provided herein prevent or obstruct the binding of gp120 to CD4 or chemokines (e.g. CCR5 and CXCR4). In one embodiment, HIV neutralizing antibodies provided herein neutralize more than one genetic subtype of HIV isolates.

Methods of Generating HIV-1-specific tAbs

In one aspect, provided herein are methods for generating HIV-1-specific tAbs that induce significant neutralization of HIV isolates. HIV-1-specific tAbs provided herein are generated by screening a library of antibodies that bind to native HIV envelope glycoproteins, and selecting the antibody that enhances binding affinity and/or neutralization activity of a second antibody. In one embodiment, the second antibody is a CD4-induced (CD4i) antibody, such as for example, X5, m9, and m16.

In one embodiment, the method comprises:
a) providing a first antibody that binds to one or more epitopes of native HIV envelope glycoproteins (Env);
b) contacting the first antibody with HIV isolates, thereby generating an antibody-Env complex;
c) contacting the antibody-Env complex with a second antibody that is capable of neutralizing HIV isolates; and
d) selecting the first antibody as a HIV-1-specific transforming antibody (tAb) if upon binding of the second antibody to the antibody-Env complex, the second antibody exhibits enhanced neutralization activity against the antibody-Env complex as compared to against the HIV-1 isolates alone. Antibodies with broad neutralization activity against HIV isolates can be determined using pseudovirus neutralization assays, which are known in the art.

In one embodiment, the library of antibodies can be constructed using mRNA or total RNA of peripheral blood mononuclear cells (PBMCs) and/or lymphocytic tissues (e.g. bone marrow, spleen) of HIV-infected or non-infected human or animal subjects. In one embodiment, the antibody library is derived from HIV-1 long-term nonprogressors (LTNPs), whose sera contain high titers of HIV-1-specific, broadly cross-reactive mAbs. In one embodiment, the library of antibodies is screened for specificity for HIV Env structure. In one embodiment, the library is screened for specificity for gp120 of native HIV-1 Env structure. In one embodiment, phage-displayed antibody libraries are panned against native HIV-1 Env-derived antigens using sequential antigen panning and/or competitive panning techniques. In one embodiment, the library of antibodies can be generated by isolating B cells from uninfected or HIV-1 infected human subjects or animals, and immortalizing the B cells with Epstein-Barr Virus (EBV). In one embodiment, the library of antibodies can also be generated using standard methods of recombinant DNA technology, which are well known in the art. In one embodiment, recombinant antibodies can be manipulated to improve therapeutic properties such as binding specificity, affinity, half-life, neutralization activity, and lack of immunogenicity.

Techniques of sequential antigen panning and/or competitive panning techniques are described in Yun-Mei Zhang et al., *J. Immunol. Met.*, 283 (1-2), 17-25 (2003); Yun-Mei Zhang et al. *J. Virol.*, 78 (17), 9233-9242 (2004); Yun-Mei Zhang et al., *J. Mol. Biol.*, 335(1), 209-219 (2004); Yun-Mei Zhang et al., *Curr. Pharm. Des.*, 13 (2), 203-212 (2007); Yun-Mei Zhang et al., *J. Immunol. Met.*, 317 (1-2), 21-30 (2006).

In one embodiment, antibodies are screened for binding specificity for HIV-1 envelope glycoproteins or HIV-1 Env-derived antigens. In one embodiment, antibodies are screened for the ability to enhance binding affinity of CD4i antibodies to gp120. Methods for determining antibody binding affinity such as the enzyme-linked immunosorbent assay (ELISA) are well known in the art, as are described in Receptor Binding Techniques Methods in Molecular Biology. 106. ed. M. Keen. Humana Press, 1999; Brooks et al. (1998) *Cell* 92:391-400; Brooks et al. (1996) *Cell* 85:683-693; and Brooks et al. (1993) *J. Cell. Biol.* 122:1351-1359.

Antibodies and Production of Antibodies

Antibodies provided herein can be in any forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, *J. Immunol. Methods* 231:177 189, 1999); fusion constructs containing an antibody or antibody fragment (e.g., a fusion protein containing a fragment of CD4, e.g., sCD4 (Salzwedel et al. *J. Virol.* 74:326 333, 2000); and human or humanized immunoglobulin molecules or fragments thereof.

Antibodies provided herein can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments called Fab fragments, each with a single antigen binding site, and a residual "Fc" fragments, so-called for its ability to crystallize readily. Pepsin treatment of an antibody yields an F(ab')$_2$ fragment that has two antigen binding portions which are capable of cross-linking antigen, and a residual other fragment (which is termed pFc'). Additional fragments can include diabodies, linear antibodies, single-chain antibody molecules, and multispecific antibodies formed from antibody fragments.

Provided herein are fusion constructs wherein the antibody, or fragment thereof, may be fused to one or more additional entities. The additional entity(ies) may be for example linkers, toxins, carriers, solid supports, and/or detectable molecules. In this context the binding portion may consist of or consist essentially of the antibody.

Antibodies provided herein include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

The polyclonal sera generated by the immunization of experimental animals undergo an initial screen for virus inhibition. Antiviral activity is evaluated in both cell-cell fusion and neutralization assays. In this format, a representative sample of lab adapted and primary virus isolates is used. Both assays are carried out according to protocols described previously (Wild, C., et al., *Proc. Natl. Acad Sci. USA* 89:10537-10541 (1992); Wild, C., et al., *Proc. Natl. Acad. Sci. USA* 91:12676-12680 (1994); Wild, C., et al., *Proc. Natl. Acad. Sci. USA* 91:9770-9774 (1994)). Samples are also screened by ELISA to characterize binding. The antigen panel includes all experimental immunogens. Animals with sera samples which test positive for binding to one or more experimental immunogens are candidates for use in MAb production. Following this initial screen, one animal representing each experimental immunogen is selected for monoclonal antibody production. The criteria for this selection is based on transforming antibody titers and in the absence of transformation, binding patterns against the panel of structured immunogens.

Monoclonal antibodies provided herein can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

Hybridoma supernatants are screened by ELISA, against structured and non-structured peptides and recombinants. Samples that are ELISA negative or weakly positive are further characterized for IgG. If IgG is present the material is screened in the biophysical and biological assays. Strongly positive samples are screened for their ability to neutralize virus and bind envelope. The experimental material can be further tested against a panel representing the spectrum of HIV-1 isolates. These isolates include lab adapted and primary virus strains, syncytium and non-syncytium inducing isolates, virus representing various geographic subtypes, and viral isolates which make use of the range of second receptors during virus entry. These neutralization assays employ either primary cell and cell line targets as required.

Antibodies are characterized in detail for their ability to bind HIV envelope under various conditions. The native envelop undergo some interaction which triggers a conformational change i.e., binding CD4 and/or co-receptor in order to expose these epitopes. For detection of antibody binding to native envelope, immunoprecipitations on Env-expressing cells and virions, both intact and lysed are performed using non-ionic detergents (Furata, R A et al., *Nat. Struct. Biol.* 5(4):276-279 (1997); White, J. M. and I. A. Wilson, *J. Cell Biol.* 105:2887-2894 (1987); Kemble, G. W., et al., *J. Virol.* 66:4940-4950 (1992)). Antibody binding to cell lysates and intact virions are also assayed in an ELISA format. Flow cytometry experiments are performed to determine binding to envelope expressing cells. Cross-competition experiments using other mapped Mabs, human sera, and peptides can also be performed. To characterize "triggers" to the conformational change, antibody binding to virus in the presence and absence of both sCD4 and target cells can be compared (White, J. M. and I. A. Wilson, *J. Cell Biol.* 105:2887-2894 (1987); Kemble, G. W., et al., *J. Virol.* 66:4940-4950 (1992)). Because the gp41 regions are highly conserved, epitope exposure using several different envelopes can be compared to discern possible differences in structure between primary, lab-adapted and genetically diverse virus isolates.

The monoclonal antibodies may also be made by recombinant DNA methods, such as those described in U.S. Pat. No. 4,816,567 (Cabilly et al.). DNA encoding the monoclonal antibodies provided herein can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 (Burton et al.) and U.S. Pat. No. 6,096,441 (Barbas et al.). Recombinant antibodies, antibody fragments, and fusions and polymers thereof can be expressed in vitro or in prokaryotic cells (e.g., bacteria) or eukaryotic cells (e.g., yeast, insect, or mammalian cells) and further purified, as necessary, using well known methods (see, e.g., Sambrook et al. Molecular Cloning: a Laboratory Manual, Cold Spring Harbor Laboratory Press (1989); and Ausubel et al., Current Protocols in Molecular Biology, John Wiley & Sons, New York, N.Y., 2001, which is updated quarterly).

Antibodies provided herein include human and humanized antibodies. The human antibodies provided herein are prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86 95, 1991). Human antibodies provided herein (and fragments thereof) are also be produced using phage display libraries (Hoogenboom et al., *J. Mol. Biol.*, 227:381, 1991; Marks et al., *J. Mol. Biol.*, 222:581, 1991; and C. F. Barbas, D. R. Burton, J. K. Scott, G. J. Silverman, *Phage Display: A Laboratory Manual*, Cold Spring Harbor Laboratory Press, Cold Spring Harbor, N.Y., 2001).

In one embodiment, the humanized antibodies provided herein are derived from animal subjects such as mouse, rabbit, and etc. Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

Methods for humanizing non-human antibodies are well known in the art. For example, humanized antibodies can be generated according to the methods of Winter and co-workers (Jones et al., *Nature*, 321:522 525 (1986), Riechmann et al., *Nature*, 332:323 327 (1988), Verhoeyen et al., *Science*, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

If desired, the antibodies provided herein can be modified in any suitable process. For example, the binding affinity of the antibodies can be increased via various methods known in the art. For example, binding characteristics can be improved by direct mutation, methods of affinity maturation, phage display, or chain shuffling within the nucleic acids encoding the antibody molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol. Bio.* 254, 392-403; Hawkins et al. (1992) *J. Mol. Bio.* 226, 889-896; or Low et al. (1996) *J. Mol. Bio.* 250, 359-368). Methods known in the art include for example, Marks et al. *BioTechnology*, 10:779-783 (1992) describes affinity maturation by VH and VL domain shuffling; random mutagenesis of CDR and/or framework residues is described by Barbas et al. *Proc. Natl. Acad. Sci., USA* 91:3809-3813 (1994); Schier et al. *Gene*, 169:147-155 (1995); Yelton et al. *J. Immunol.*, 155:1994-2004 (1995); Jackson et al., *J. Immunol.*, 154(7):3310-3319 (1995); and Hawkins et al, *J. Mol. Biol.*, 226:889-896 (1992).

In one embodiment, strategies for antibody optimization are carried out using random mutagenesis. In these cases, positions are chosen randomly, or amino acid changes are made using simplistic rules. For example all residues may be mutated to alanine, referred to as alanine scanning. WO 9523813 (which is hereby incorporated by reference in its entirety) teaches in vitro methods of increasing antibody affinities utilizing alanine scanning mutagenesis. Alanine scanning mutagenesis can also be used, for example, to map the antigen binding residues of an antibody (Kelley et al., 1993, *Biochemistry* 32:6828-6835; Vajdos et al., 2002, *J. Mol. Biol.* 320:415-428). Sequence-based methods of affinity maturation (see, U.S. Pat. Application No. 2003/022240 A1 and U.S. Pat. No. 2002/177170 A1, both hereby incorporated by reference in their entireties) may also be used to increase the binding affinities of antibodies.

Peptides recognized by tAbs provided herein are epitopes, antigens, antigenic fragments, peptides, immunogens, fusion construct of HIV that are recognized by tAbs.

Preferred peptides or multimers thereof, that can be employed in this aspect of the invention comprise about 6 or more amino acids, preferably about 24-56 amino acids. The peptides can be administered as a small peptide, or conjugated to a larger carrier protein such as keyhole limpet hemocyanin (KLH), ovalbumin, bovine serum albumin (BSA) or tetanus toxoid. The peptides described herein include conservative amino acid substitutions. Conserved amino acid substitutions consist of replacing one or more amino acids of the peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to the peptide from which it is derived. The peptides and conjugates may include amino acid insertions which consist of single amino acid residues or stretches of residues ranging from 2 to 15 amino acids in length. One or more insertions may be introduced into the peptide, peptide fragment, analog and/or homolog.

The peptides may include amino acid deletions of the full length peptide, analog, and/or homolog. Such deletions consist of the removal of one or more amino acids from the full-length peptide sequence, with the lower limit length of the resulting peptide sequence being 4 to 6 amino acids. Such deletions may involve a single contiguous portion or greater than one discrete portion of the peptide sequences.

The peptides may be synthesized or prepared by techniques well known in the art. See, for example, Creighton, Proteins: Structures and Molecular Principles, W.H. Freeman & Co., New York, N.Y. (1983), which is incorporated herein by reference in its entirety. Short peptides, for example, can be synthesized as a solid support or in solution. Longer peptides maybe made using recombinant DNA techniques. Here, the nucleotide sequences encoding the peptides may be synthesized, and/or cloned, and expressed according to techniques well known to those of ordinary skill in the art. See, for example, Sambrook, et al., Molecular Cloning, *A Laboratory Manual*, Vols. 1-3, Cold Spring Harbor Press, Cold Spring Harbor, N.Y. (1989).

In yet another embodiment, peptides comprising the sequences described above may be synthesized with additional chemical groups present at their amino and/or carboxy termini, such that, for example, the stability, bioavailability, and/or immunogenic activity of the peptides is enhanced.

For example, hydrophobic groups such as carbobenzoxy, dansyl, or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group t-butyloxycarbonyl, or an amido group may be added to the peptides' carboxy termini.

Also provided herein is a method for preparing target peptides that involves the use of a bacterial expression vector. Novel fusion peptides (conjugates) are also provided, as are vectors, host cells and recombinant methods for producing the same. Also provided herein are isolated nucleic acid molecules comprising a polynucleotide encoding the fusion peptide.

Also provided herein are recombinant vectors, which include the isolated nucleic acid molecules, and to host cells containing the recombinant vectors, as well as to methods of making such vectors and host cells and for using them for production of fusion peptides or peptides by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as that described herein. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods. In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

The fusion peptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Depending upon the host employed in a recombinant production procedure, the polypeptides provided herein may be glycosylated or may be non-glycosylated. In addition, polypeptides provided herein may also include an initial modified methionine residue, in some cases as a result of host-mediated processes.

Therapeutic Compositions for Prevention and/or Treatment of HIV Infection

Also provided are therapeutic compositions, comprising a therapeutically effective amount of HIV-1-specific tAbs and antigens. The therapeutic compositions are useful for treatment and/or prevention of HIV infection. In an embodiment, the compositions provided herein are used as a vaccine composition to prevent individuals from acquiring HIV infection. In another embodiment, the compositions provided herein are used to treat or ameliorate HIV infection.

The term "treating," as used herein, includes but is not limited to, reducing, suppressing, inhibiting, lessening, or affecting the progression, severity, and/or scope of a condition, chance of re-occurrence or returning of a disease after a remission. In one embodiment, treating may include directly affecting or curing, suppressing, inhibiting, reducing the severity of, delaying the onset of, reducing symptoms associated with an infection, or a combination thereof. In another embodiment, treating includes delaying progression, expediting remission, inducing remission, augmenting remission, speeding recovery, increasing efficacy of or decreasing resistance to alternative therapeutics, or a combination thereof.

The term "preventing," as used herein, includes but is not limited to, delaying the onset of symptoms, preventing relapse to a disease, decreasing the number or frequency of relapse episodes, increasing latency between symptomatic episodes, or a combination thereof.

A therapeutically effective amount is an amount of a therapeutic substance provided herein (e.g. antibody and antigen) sufficient to prevent a subject from or produce a measurable treatment effect on HIV infection.

In an embodiment, the therapeutic compositions provided herein further comprise tAb-antigens that are recognized by tAbs, CD4, sCD4, an immunogenic portion of an envelope protein of HIV, Env-CD4 complex, CD4i Abs (e.g. E51, 31H, 23e, 21c, 17b, 48d, Fab X5, 412d, 19e, ED47, ED49, m12, m6, and m9) and/or active fragments and fusion proteins thereof.

Also provided herein are therapeutic compositions useful for practicing the therapeutic methods described herein. Therapeutic compositions provided herein contain a physiologically tolerable carrier together with a therapeutically effective amount of an antibody as described herein, dissolved or dispersed therein as an active ingredient. In one embodiment, the therapeutic composition is not immunogenic or has reduced immunogenicity when administered to a mammal or human patient for therapeutic purposes.

A therapeutically effective amount of an antibody provided herein in the form of a monoclonal antibody is typically an amount such that when administered in a physiologically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antibody is in the form of an active fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The vaccines provided herein may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the conjugate vaccine has suitable solubility properties. The vaccines may be in the form of single dose preparations or in multi-dose flasks which can be used for mass vaccination programs. Reference is made to Remington's Pharmaceutical Sciences, Osol, ed., Mack Publishing Co., Easton, Pa. (1980), and New Trends and Developments in Vaccines, Voller, et al., eds., University Park Press, Baltimore, Md. (1978), for methods of preparing and using vaccines.

The vaccines provided herein may further comprise adjuvants which enhance production of HIV-specific antibodies. Such adjuvants include, but are not limited to, various oil formulations such as Freund's complete adjuvant (CFA), stearyl tyrosine (ST, see U.S. Pat. No. 4,258,029), the dipeptide known as MDP, saponins and saponin derivatives, such as Quil A and QS-21, aluminum hydroxide, and lymphatic cytokine. Preferably, an adjuvant will aid in maintaining the secondary and quaternary structure of the immunogens.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The vaccine may be absorbed onto the aluminum hydroxide from which it is slowly released after injection. The vaccine may also be encapsulated within liposomes according to Fullerton, U.S. Pat. No. 4,235,877, or mixed with or liposomes or lipid mixtures to provide an environment similar to the cell surface environment.

In another preferred embodiment, one or more peptides are combined with other peptides that are used to vaccinate animals.

In one embodiment, provided herein is a method of inducing an immune response in an animal comprising administering to the animal the vaccine provided herein in an amount effective to induce an immune response. Optionally, the vaccine may be coadministered with effective amounts of other peptides as mentioned above to generate multiple immune responses in the animal.

Compositions provided herein are useful as vaccines to induce active immunity towards antigens in subjects. Any animal that may experience the beneficial effects of the compositions provided herein within the scope of subjects that may be treated. The subjects are preferably mammals, and more preferably humans.

The administration of the vaccine may be for either a "prophylactic" or "therapeutic" purpose. When provided prophylactically, the vaccine(s) are provided in advance of any symptoms of HIV infection, or in advance of any known exposure to HIV. The prophylactic administration of the vaccine(s) serves to prevent or attenuate any subsequent infection. When provided therapeutically, the vaccine(s) is provided upon or after the detection of symptoms which indicate that an animal may be infected with HIV, or upon or after exposure to the virus. The therapeutic administration of the vaccine(s) serves to attenuate any actual infection, for example as measured by improving the symptoms of a subject, or by reducing the level of viral replication. Thus, the vaccines, may be provided either prior to the onset of infection (so as to prevent or attenuate an anticipated infection) or after the initiation of an actual infection.

Routes of Administration

The antibodies provided herein are administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antibodies, and derivatives thereof can be administered intravenously, intraperitoneally, intramuscularly, subcutaneously, intracavity, transdermally, topically, intraocularly, orally, intranasally, and can be delivered by peristaltic means.

The therapeutic compositions containing an antibody provided herein are conventionally administered intravenously, as by injection of a unit dose, for example. The term "unit dose" when used in reference to a therapeutic composition provided herein refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Following are examples that illustrate certain embodiments provided herein. These examples should not be construed as limiting. All percentages are by weight and all solvent mixture proportions are by volume unless otherwise noted.

Example 1—Enhancement of Neutralization Activity of X5 Against HIV Isolates

HIV-1-specific tAbs provided herein can lead to enhanced binding affinity of CD4i Abs to gp120 and enhanced neutralization activity of CD4i Abs against HIV isolates. Enhancement of binding affinity and neutralization activity induced by tAbs is stronger than that which is induced by A32.

Figure 1:
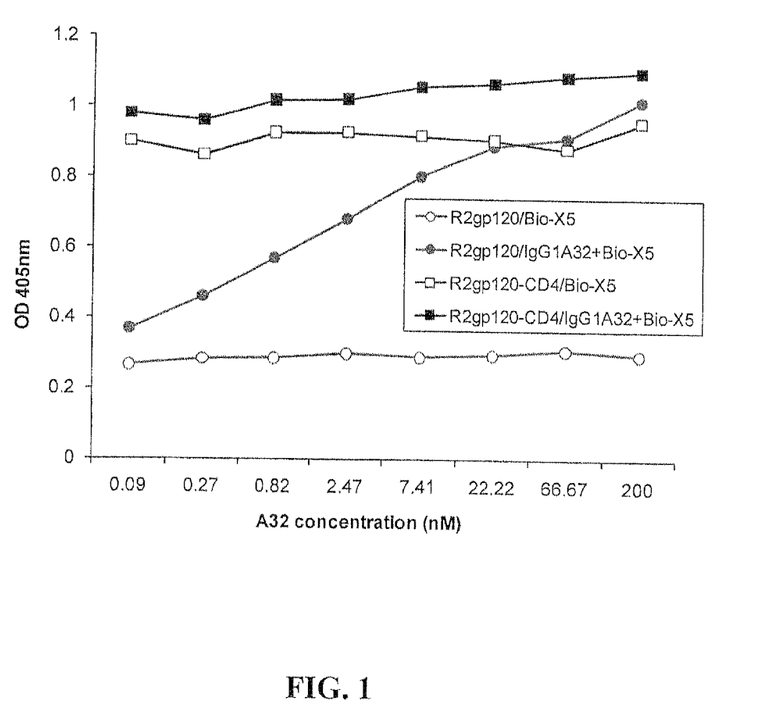
FIG. 1 shows enhanced binding affinity of CD4i Ab X5 to gp120 by human anti-gp120 mAb A32.
Figure 2:
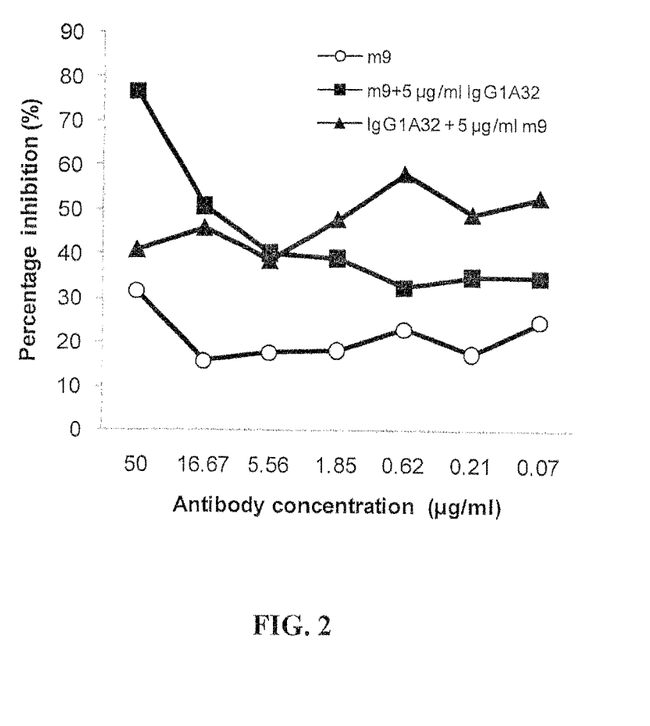
FIG. 2 shows that human anti-gp120 mAb A32 enhances neutralization activity of CD4i Ab scFv m9 against HIV-1 isolate JRFL.

FIG. 1 shows enhanced binding of CD4i Ab X5 to gp120 by human anti-gp120 mAb A32. Specifically, Maxi-sorp ELISA plates were coated with 1 μg/ml of $gp120_{R2}$ or 1 μg/ml $gp120_{R2}$-CD4, respectively. Then, 3-fold serially diluted A32 and biotinylated IgG1 X5 at a fixed concentration capable of producing 50-70% of maximal binding to gp120 were added simultaneously. Gp120-bound X5 Abs were detected using HRP-avidin as the $2^{nd}$ antibody and ABTS as the substrate. The optical density was measured at 450 nm. The results show that A32 mAbs and sCD4 both lead to enhanced binding affinity of X5 to gp120. In addition, the combination of A32 mAbs and sCD4 produces addition effect in enhancing the X5-gp120 binding affinity, evidencing that epitopes bound by A32 and sCD4 do not overlap. The results of pseudovirus neutralization assays as shown in FIG. 2 further demonstrate that human anti-gp120 mAb A32 can enhance neutralization activity of CD4i Ab scFv m9 against HIV-1 isolate JRFL. Specifically, the neutralization activities of m9 (three-fold serially diluted, control), m9 (three-fold serially diluted) and 5 μg/ml of A32, and A32 (three-fold serially diluted) and 5 μg/ml of m9 (constant) were tested. The results show that A32 enhanced the neutralization activity of m9. In addition, A32-induced enhanced neutralization activity is independent of A32 concentration, as an increase in A32 concentration did not result in increased neutralization against HIV isolates.

Example 2-Enhancement of Neutralization Activity of M9 with Fab A32

Figure 3:
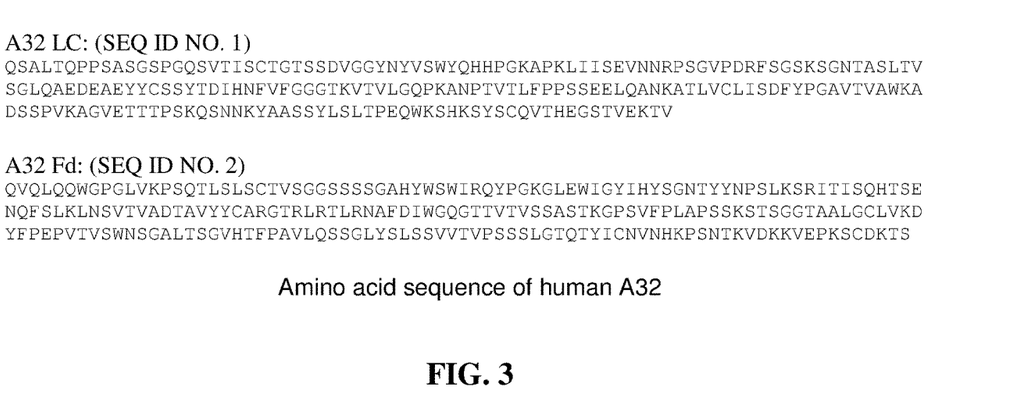
FIG. 3 shows an amino acid sequence of human Fab A32 (H32).

Human mAb Fab A32 was cloned from EBV-immortalized human B cell lines (FIG. 3). Fab A32 was tested for enhancing m9 neutralization in pseudovirus assay and found that recombinant Fab A32 retained the ability to enhance the neutralization activity of CD4i antibody m9 in neutralizing HIV-1 clade B isolate JRFL (Table 1). A mutant library of Fab A32 is being constructed to select A32 mutants that have increased ability in enhancing the neutralizing potency of CD4i antibodies.

TABLE 1

Percentage neutralization of m9 in combination with Fab A32.

| Antibody combination | | Percentage |
|---|---|---|
| m9 (μg/ml) | Fab A32 (μg/ml) | neutralization (%) |
| 5 | 20 | 51 |
| 5 | 10 | 45 |
| 5 | 5 | 26 |
| 5 | 2.5 | 17 |

Example 3

Two immune antibody Fab libraries were constructed using mRNA isolated from the PBMCs obtained from two HIV-1-infected individuals whose serum exhibited broad and potent neutralization activity. The two Fab libraries have a size of 10 exp 8-9 individual clones. These two libraries are being panned for A32-like antibodies and characterize isolated antibodies for enhancing the binding and neutralizing activities of CD4i antibodies.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope provided herein without limitation thereto.

The invention claimed is:

1. A method for screening or generating a HIV-1-specific transforming antibody (tAb) useful for prevention and/or treatment of HIV-1 infection, comprising the steps of:
   a) providing a first antibody fragment that binds to one or more epitopes of a native, HIV envelope glycoprotein (Env), wherein the first antibody fragment is selected from the group consisting of a Fab fragment, a F(ab')$_2$ fragment and a Fab' fragment;
   b) contacting the first antibody fragment with HIV isolates, thereby generating an antibody-Env complex;
   c) contacting the antibody-Env complex with a second antibody that is capable of neutralizing HIV isolates;
   d) selecting the first antibody fragment if upon binding of the second antibody to the antibody-Env complex, the second antibody exhibits enhanced neutralization activity against the antibody-Env complex as compared to neutralization activity of the second antibody against the HIV-1 isolates alone; and
   (e) converting the selected first antibody fragment to IgG.

2. The method according to claim 1, wherein the first antibody fragment binds to an epitope on gp120 or gp41.

3. The method according to claim 2, wherein the first antibody fragment binds to a site that is or overlaps with CD4 binding site.

4. The method according to claim 1, wherein the first antibody fragment that binds to one or more epitopes of native HIV envelope glycoprotein is generated using recombinant DNA technology, phage display technology, sequential antigen panning, competitive antigen panning, ELISA or any combination thereof.

5. The method according to claim 1, wherein the first antibody fragment is derived from mRNA or total RNA of peripheral blood mononuclear cells (PBMCs) and/or lymphocytic tissues of an HIV-infected subject.

6. The method according to claim 1, the HIV isolates comprises HIV-1 Clade A, B, C, D, E, F, G, H, or any combination thereof.

7. The method according to claim 1, wherein the second antibody is a CD4i Ab.

8. The method according to claim 7, wherein the second antibody is E51, 31H, 23e, 21c, 17b, 48d, X5, 412d, 19e, ED47, ED49, m12, m6, or m9.

9. The method according to claim 8, wherein the second antibody is X5 or m9.

10. The method according to claim 1, further comprising selecting the first antibody fragment as a HIV-1-specific transforming antibody (tAb) if upon binding of the second antibody to the antibody-Env complex, the second antibody exhibits enhanced neutralization activity against the antibody-Env complex as compared to neutralization activity of the second antibody against the HIV-1 isolates that are incubated with A32 when A32 is used in place of the first antibody fragment.

11. The method according to claim 1, wherein the neutralization activity of the second antibody is detected using pseudovirus neutralization assay.

12. The method according to claim 1, further comprising selecting the first antibody fragment as a HIV-1-specific transforming antibody (tAb) if upon binding of the second antibody to the antibody-Env complex, the second antibody exhibits enhanced binding affinity to the antibody-Env complex as compared to the binding affinity of the second antibody to HIV-1 isolates alone.

* * * * *

SEQUENCE LISTING

<160> NUMBER OF SEQ ID NOS: 8

<210> SEQ ID NO 1
<211> LENGTH: 210
<212> TYPE: PRT
<213> ORGANISM: Homo Sapiens

<400> SEQUENCE: 1

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

-continued

```
Asn Tyr Val Ser Trp Tyr Gln His Pro Gly Lys Ala Pro Lys Leu
             35                  40                  45

Ile Ile Ser Glu Val Asn Asn Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Glu Tyr Tyr Cys Ser Ser Tyr Thr Asp Ile
                 85                  90                  95

His Asn Phe Val Phe Gly Gly Thr Lys Val Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
            195                 200                 205

Thr Val
    210

<210> SEQ ID NO 2
<211> LENGTH: 230
<212> TYPE: PRT
<213> ORGANISM: Homo Sapiens

<400> SEQUENCE: 2

Gln Val Gln Leu Gln Gln Trp Gly Pro Gly Leu Val Lys Pro Ser Gln
 1               5                  10                  15

Thr Leu Ser Leu Ser Cys Thr Val Ser Gly Gly Ser Ser Ser Ser Gly
             20                  25                  30

Ala His Tyr Trp Ser Trp Ile Arg Gln Tyr Pro Gly Lys Gly Leu Glu
             35                  40                  45

Trp Ile Gly Tyr Ile His Tyr Ser Gly Asn Thr Tyr Tyr Asn Pro Ser
 50                  55                  60

Leu Lys Ser Arg Ile Thr Ile Ser Gln His Thr Ser Glu Asn Gln Phe
 65                  70                  75                  80

Ser Leu Lys Leu Asn Ser Val Thr Val Ala Asp Thr Ala Val Tyr Tyr
                 85                  90                  95

Cys Ala Arg Gly Thr Arg Leu Arg Thr Leu Arg Asn Ala Phe Asp Ile
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

-continued

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr Ser
225                 230

<210> SEQ ID NO 3
<211> LENGTH: 14
<212> TYPE: PRT
<213> ORGANISM: Homo Sapiens

<400> SEQUENCE: 3

Thr Gly Thr Ser Ser Asp Val Gly Gly Tyr Asn Tyr Val Ser
1               5                   10

<210> SEQ ID NO 4
<211> LENGTH: 7
<212> TYPE: PRT
<213> ORGANISM: Homo Sapiens

<400> SEQUENCE: 4

Glu Val Asn Asn Arg Pro Ser
1               5

<210> SEQ ID NO 5
<211> LENGTH: 10
<212> TYPE: PRT
<213> ORGANISM: Homo Sapiens

<400> SEQUENCE: 5

Ser Ser Tyr Thr Asp Ile His Asn Phe Val
1               5                   10

<210> SEQ ID NO 6
<211> LENGTH: 7
<212> TYPE: PRT
<213> ORGANISM: Homo Sapiens

<400> SEQUENCE: 6

Ser Gly Ala His Tyr Trp Ser
1               5

<210> SEQ ID NO 7
<211> LENGTH: 16
<212> TYPE: PRT
<213> ORGANISM: Homo Sapiens

<400> SEQUENCE: 7

Tyr Ile His Tyr Ser Gly Asn Thr Tyr Tyr Asn Pro Ser Leu Lys Ser
1               5                   10                  15

<210> SEQ ID NO 8
<211> LENGTH: 13
<212> TYPE: PRT
<213> ORGANISM: Homo Sapiens

<400> SEQUENCE: 8

Gly Thr Arg Leu Arg Thr Leu Arg Asn Ala Phe Asp Ile
1               5                   10